US007069792B2

(12) United States Patent
Casad et al.

(10) Patent No.: US 7,069,792 B2
(45) Date of Patent: Jul. 4, 2006

(54) JOINT SEALANT ADHESION INDICATOR

(76) Inventors: Donald F. Casad, 2303 McElroy Pl., Puyallup, WA (US) 98371-4805; Daniel N. Huff, 19153 - Shoshone, Bend, OR (US) 97702; Dale R. Herbert, 8505 Woodlawn Ave., SW., Lakewood, WA (US) 98499

( * ) Notice: Subject to any disclaimer, the term of this patent is extended or adjusted under 35 U.S.C. 154(b) by 454 days.

(21) Appl. No.: 10/215,683

(22) Filed: Aug. 8, 2002

(65) Prior Publication Data

US 2004/0123669 A1 Jul. 1, 2004

(Under 37 CFR 1.47)

Related U.S. Application Data

(60) Provisional application No. 60/311,011, filed on Aug. 8, 2001.

(51) Int. Cl.
*G01N 3/00* (2006.01)

(52) U.S. Cl. .......................................................... 73/807

(58) Field of Classification Search ..................... 73/37, 73/820, 807

See application file for complete search history.

(56) References Cited

U.S. PATENT DOCUMENTS

| | | | | |
|---|---|---|---|---|
| 4,043,179 A | | 8/1977 | Ingle, Jr. | |
| 5,078,005 A | | 1/1992 | Krempel et al. | |
| 5,127,260 A | | 7/1992 | Robertson | |
| 5,315,861 A | | 5/1994 | Egan et al. | |
| 5,351,562 A | | 10/1994 | Scott | |
| 5,454,260 A | | 10/1995 | Wang | |
| 5,705,736 A | | 1/1998 | McCranie | |
| 5,744,703 A | | 4/1998 | Krenceski et al. | |
| 5,841,034 A | * | 11/1998 | Ball | 73/800 |
| 6,513,369 B1 | | 2/2003 | Chew | |
| 6,711,938 B1 | * | 3/2004 | Huff | 73/37 |
| 2003/0037595 A1 | | 2/2003 | Huff | |

FOREIGN PATENT DOCUMENTS

WO WO 03/012400 A1 2/2003

OTHER PUBLICATIONS

Lin–Act, Cylinder Division (USA), Des Plaines, IL, Stainless Steel Body Air Cylinder Series SR & SRM Catalogue LA 0960 —specification sheet, Series C'85.

* cited by examiner

*Primary Examiner*—Edward Lefkowitz
*Assistant Examiner*—Octavia Davis
(74) *Attorney, Agent, or Firm*—R. Reams Goodloe, Jr.

(57) ABSTRACT

Apparatus for locating adhesive failure of sealant joints. Useful for determination of the quality of sealant joints in structures, especially curtain wall buildings. A substantially constant pressure probe is utilized to displace roughly a middle third of a sealant bead that is located along a sealant joint having longitudinal axis and spanning a gap between adjacent substrates, using a predetermined force calibrated to provide a preselected elongation of a particular type of sealant. The testing apparatus has a frame, a first fluid cylinder having an first end wall, a first tubular cylinder wall, a first piston, and a first shaft. The first shaft is response to movement of the first piston. The first shaft has a probe affixed thereto. A second fluid cylinder is provided having an internal pressure equalization chamber defined by a second end wall, a second tubular cylinder wall, a second piston, and a fluid supply port for receiving a substantially constant pressure fluid supply to the internal pressure equalization chamber. Movement of the first piston transfers fluid pressure to the internal pressure equalization chamber of the second piston, thereby maintaining a substantially constant pressure on the first piston, and thus maintaining a substantially constant reaction force on the probe.

20 Claims, 15 Drawing Sheets

FIG. 8
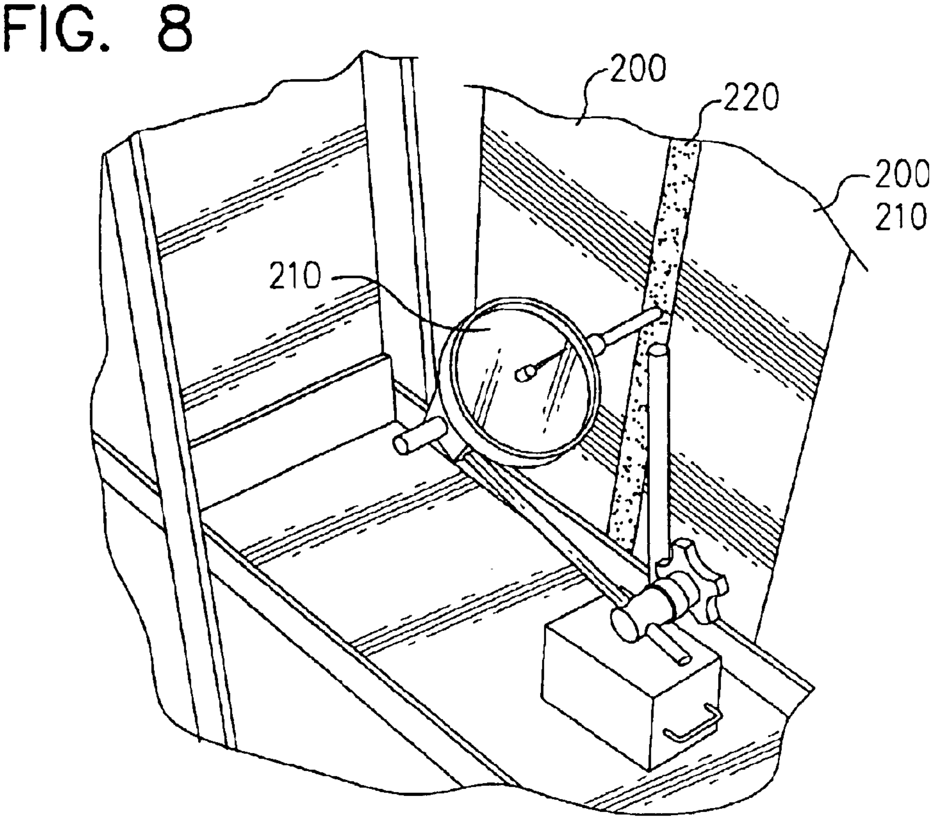
FIG. 9
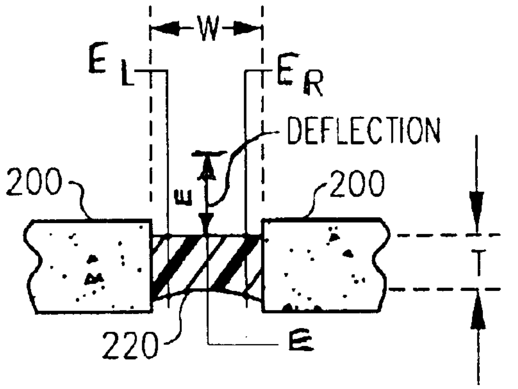
FIG. 10
TEST JOINT WIDTHS:
| | | |
|---|---|---|
| A | 1" W | 1/2" T |
| B | 3/4" W | 1/4" T |
| C | 1/2" W | 1/4" T |
| D | 7/8" W | 1/4" T |

FIG. 11

| JOINT DIMENSIONS- IN INCHES | | | | | | JT AVERAGE CROSS SECTION WIDTH | RATIO OF AVE. JT. DEPTH AT SUBSTRATE TO DEPTH AT CENTER OF JT. |
|---|---|---|---|---|---|---|---|
| SAMPLE | | W | DL | D | DR | (DL+DR+D)/3 | (DL+DR)/2D |
| A | TOP<br>CENTER<br>BOTTOM | Ø.981<br>Ø.984<br>Ø.992 | Ø.403<br>Ø.440<br>Ø.458 | Ø.332<br>Ø.426<br>Ø.392 | Ø.410<br>Ø.495<br>Ø.492 | Ø.382<br>Ø.454<br>Ø.447 | 1.224<br>1.097<br>1.212 |
| B | TOP<br>CENTER<br>BOTTOM | Ø.748<br>Ø.755<br>Ø.750 | Ø.412<br>Ø.382<br>Ø.480 | Ø.342<br>Ø.348<br>Ø.375 | Ø.386<br>Ø.415<br>Ø.484 | Ø.380<br>Ø.382<br>Ø.446 | 1.167<br>1.145<br>1.285 |
| C | TOP<br>CENTER<br>BOTTOM | Ø.460<br>Ø.462<br>Ø.472 | Ø.350<br>Ø.372<br>Ø.392 | Ø.240<br>Ø.275<br>Ø.287 | Ø.324<br>Ø.390<br>Ø.383 | Ø.305<br>Ø.346<br>Ø.354 | 1.404<br>1.385<br>1.350 |
| D | BOTTOM | Ø.755 | Ø.275 | Ø.206 | Ø.277 | Ø.253 | 1.340 |
| | CENTER<br>BOTTOM | Ø.745<br>Ø.743 | Ø.255<br>Ø.248 | Ø.203<br>Ø.200 | Ø.246<br>Ø.245 | Ø.253<br>Ø.231 | 1.234<br>1.233 |

FIG. 12

| | DEFLECTION (HUNDRETHS OF AN INCH) | | | | | | |
|---|---|---|---|---|---|---|---|
| PSI 15# | PASS 1 | PASS 2 | PASS 3 | PASS 4 | PASS 5 | PASS 6 | AVERAGE |
| TOP | 16.000 | 14.000 | 14.000 | 16.000 | 18.000 | 18.000 | 16.000 |
| CENTER | 11.000 | 14.000 | 14.000 | 14.000 | 14.000 | 15.000 | 13.667 |
| BOTTOM | 12.000 | 12.000 | 15.000 | 14.000 | 14.000 | 12.000 | 13.167 |
| AVERAGE | 13.000 | 13.333 | 14.333 | 14.667 | 15.333 | 15.000 | |
| PSI 20# | PASS 1 | PASS 2 | PASS 3 | PASS 4 | PASS 5 | PASS 6 | AVERAGE |
| TOP | 19.000 | 19.000 | 20.000 | 18.000 | 19.000 | 22.000 | 19.500 |
| CENTER | 19.000 | 20.000 | 20.000 | 18.000 | 19.000 | 20.000 | 19.333 |
| BOTTOM | 17.000 | 19.000 | 16.000 | 13.000 | 18.000 | 18.000 | 16.833 |
| AVERAGE | 18.333 | 19.333 | 18.667 | 16.333 | 18.667 | 20.000 | |
| PSI 25# | PASS 1 | PASS 2 | PASS 3 | PASS 4 | PASS 5 | PASS 6 | AVERAGE |
| TOP | 22.000 | 23.000 | 24.000 | 23.000 | 23.000 | 24.000 | 23.167 |
| CENTER | 22.000 | 24.000 | 23.000 | 24.000 | 23.000 | 25.000 | 23.500 |
| BOTTOM | 17.000 | 19.000 | 21.000 | 20.000 | 20.000 | 18.000 | 19.167 |
| AVERAGE | 20.333 | 22.000 | 22.667 | 22.333 | 22.000 | 22.333 | |

NOTES:

| | |
|---|---|
| JOINT LABEL | A |
| JOINT WIDTH | 1" |
| MTL THICKNESS | 1/2" |
| SEALANT | DOW |
| WHEEL NO. | #1 |

FIG. 13

| | # | WHEEL SIZE WIDTH, IN (WW) |
|---|---|---|
| ROLLER WHEEL SIZES | #1 | 0.182 |
| | #2 | 0.255 |
| | #3 | 0.290 |
| | #4 | 0.382 |
| | #5 | 0.427 |
| | #6 | 0.482 |

SPECIMEN "A"

| | |
|---|---|
| JOINT WIDTH (INCH) | 1.000 INCH |
| REQ'D TEST DEFLECTION (50% OF JOINT THICKNESS) | 0.250 INCH |

AVERAGE DEFLECTION (1/100 INCH)

| WHEEL SIZE (in) | 30 PSI | 25 PSI | 20 PSI | 15 PSI |
|---|---|---|---|---|
| REQ'D | 25.000 | 25.000 | 25.000 | 25.000 |
| 0.182 | | 21.94 | 18.56 | 14.28 |
| 0.255 | | 22.89 | 17.78 | 13.67 |
| 0.290 | | 24.61 | 16.61 | 12.00 |
| 0.382 | | 20.94 | 14.33 | 12.61 |
| 0.427 | | 19.94 | 14.89 | 11.94 |
| 0.482 | 25.22 | 21.17 | 15.00 | 10.17 |

| # | WHEEL SIZE (IN) |
|---|---|
| #1 | 0.182 |
| #2 | 0.255 |
| #3 | 0.290 |
| #4 | 0.382 |
| #5 | 0.427 |
| #6 | 0.482 |

IMPACT OF WHEEL SIZE RELATIVE TO DEFLECTION 1" JOINT

SPECIMEN "B"

JOINT WIDTH (INCH) 5/8" = 0.625 INCH
REQ'D TEST DEFLECTION (50% OF JOINT THICKNESS) 0.156 INCH

AVERAGE DEFLECTION (1/100 INCH)

| WHEEL SIZE (in) | 30 PSI | 25 PSI | 20 PSI | 15 PSI |
|---|---|---|---|---|
| REQ'D | 15.625 | 15.625 | 15.625 | 15.625 |
| 0.182 | | 18.78 | 16.44 | 13.50 |
| 0.255 | | 21.11 | 16.72 | 15.11 |
| 0.290 | | 19.89 | 13.67 | 13.39 |
| 0.382 | | 17.78 | 14.22 | 13.00 |
| 0.427 | | 16.78 | 13.22 | 12.39 |
| 0.482 | 17.33 | 18.33 | 13.00 | 12.50 |

| # | WHEEL SIZE (IN) |
|---|---|
| #1 | 0.182 |
| #2 | 0.255 |
| #3 | 0.290 |
| #4 | 0.382 |
| #5 | 0.427 |
| #6 | 0.482 |

IMPACT OF WHEEL SIZE RELATIVE TO DEFLECTION 5/8" JOINT

SPECIMEN "C"

JOINT WIDTH (INCH) 1/2" = 0.500 INCH
REQ'D TEST DEFLECTION (50% OF JOINT THICKNESS) 0.125 INCH

AVERAGE DEFLECTION (1/100 INCH)

| WHEEL SIZE (in) | 30 PSI | 25.PSI | 20.PSI | 15 PSI |
|---|---|---|---|---|
| REQ'D | 12.500 | 12.500 | 12.500 | 12.500 |
| 0.182 | | 14.39 | 11.39 | 9.78 |
| 0.255 | | 14.83 | 11.50 | 9.61 |
| 0.290 | | | 9.67 | 8.56 |
| 0.382 | | | 7.72 | 6.17 |
| 0.427 | | | 6.11 | 4.61 |
| 0.482 | | 0.00 | 0.00 | 0.00 |

| # | WHEEL SIZE (IN) |
|---|---|
| #1 | 0.182 |
| #2 | 0.255 |
| #3 | 0.290 |
| #4 | 0.382 |
| #5 | 0.427 |
| #6 | 0.482 |

IMPACT OF WHEEL SIZE RELATIVE TO DEFLECTION 1/2" JOINT

FIG. 18

SPECIMEN "D"

JOINT WIDTH (INCH) 7/8" = 0.875 INCH
REQ'D TEST DEFLECTION (50% OF JOINT THICKNESS) 0.219 INCH

AVERAGE DEFLECTION (1/100 INCH)

| WHEEL SIZE (in) | 30 PSI | 25.PSI | 20.PSI | 15 PSI |
|---|---|---|---|---|
| REQ'D | 21.875 | 21.875 | 21.875 | 21.875 |
| 0.182 | | 37.06 | 31.39 | 22.56 |
| 0.255 | | 37.50 | 31.72 | 24.22 |
| 0.290 | | 38.00 | 29.00 | 23.83 |
| 0.382 | | 36.39 | 27.22 | 23.22 |
| 0.427 | | 32.22 | 26.78 | 21.00 |
| 0.482 | | 32.22 | 24.56 | 21.06 |

| # | WHEEL SIZE (IN) |
|---|---|
| #1 | 0.182 |
| #2 | 0.255 |
| #3 | 0.290 |
| #4 | 0.382 |
| #5 | 0.427 |
| #6 | 0.482 |

IMPACT OF WHEEL SIZE RELATIVE TO DEFLECTION 7/8" JOINT

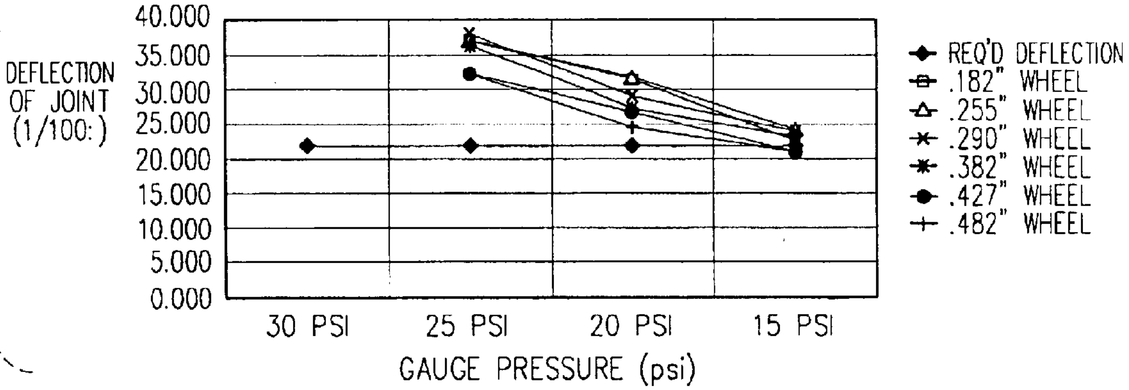

FIG. 19

SUMMARY OF COMPARISONS OF WHEEL SIZE & GAUGE PRESSURE BASED UPON GRAPHS GENERATED

| | GAUGE PRESSURE (psi) MIN | MAX | ALLOWABLE WHEEL SIZE |
|---|---|---|---|
| 1.0" JOINT | 28 | 30 | .182, .255, .290, .382, .427, .482 |
| 7/8" JOINT | 14 | 16 | .182, .255, .290, .382, .427, .482 |
| 5/8" JOINT | 22 | 23 | .290, 382, .427, .482 |
| | 17 | 18 | .182, .255 |
| 1/2" JOINT | 21 | 22 | .182, .255 |

JOINT SEALANT ADHESION INDICATOR

RELATED PATENT APPLICATIONS

This invention is related to U.S. Provisional Patent Application Ser. No. 60/311,011, filed on Aug. 8, 2001, entitled Joint Sealant Adhesion Indicator, the disclosure of which is incorporated herein in its entirety by this reference.

TECHNICAL FIELD

This invention relates to apparatus and methods for the measurement of the quality of sealant joints as applied in building construction, and more particularly, to methods and apparatus for objectively and non-destructively testing, both in the field and in the manufacturing plant, the adhesion of elastomers in joints, especially in buildings utilizing curtain wall construction.

BACKGROUND

Several methods and apparatus are known for inspecting and measuring thickness and quality of elastomeric joints, and particularly for joints in building construction. Unfortunately, a determination of the quality and thickness of such materials heretofore has been almost, if not entirely, exclusively via the use of either test specimens, or by the destructive testing of samples. In other words, no effective methods of non-destructive testing for sealant joints are currently utilized in the building construction or building inspection trades.

Consequently, the heretofore available apparatus for carrying out such inspections has been quite limited with respect to the quality or completeness of data produced therefrom, at least with respect to cost effectiveness. Quite simply, the techniques currently employed for measurement of performance of joints utilizing elastomeric materials is too intrusive for widespread use thereof.

Consequently, testing of building joint structures in response to life safety or resulting from legislative or regulatory requirements has generally been at substantial cost. Obviously, the current practice of utilizing destructive inspection techniques makes it desirable to develop a non-destructive test technique; such a development would also improve the efficiency and completeness of such inspections, while reducing costs thereof.

From the foregoing, it is clear that there is a continuing need for a simple, low cost, quickly executable non-destructive inspection apparatus which can enable semi-skilled personnel to confidently, accurately, and reliably carry out a thorough inspection utilizing an easily and simply implemented, relatively low cost methodology.

It is significant that none of the prior art methods known to us, such as those contained within the ASTM Testing Standards, are concerned with the specific problem of providing a simple, low cost apparatus and method for the quick, non-destructive determination of the performance of elastomeric joints in building structures. This problem is of significant interest to a wide variety of facilities, particularly those that have utilized curtain wall construction, and more particularly, in those high rise structures which have thousands of lineal feet of such joints in place. Thus, a continuing need exists for simple non-destructive inspection equipment that can provide a full 100% inspection data package for scanned elastomeric materials at a relatively low cost.

SUMMARY

We have developed a non-destructive, simple inspection device for inspecting elastomeric materials installed to seal joints between adjacent substrates. The elastomeric material to be inspected is traversed by a probe carriage device of the type and at an interface applied force as appropriate for the particular type of elastomeric material being inspected. The probe carriage is located in a working engagement position with respect to the elastomeric material so that the probe can effectively engage the elastomeric material to transmit force thereto at a substantially uniform level, substantially independent of the action of the workman or robotic apparatus utilized to direct the motion of the probe carriage. Thus, the probe carriage is transportably supported in a working position, by a workman or support structure in a manner that the probe displaces from a resting position the elastomeric material by the application of force thereto. Displacement of the elastomeric material resulting from passage of the probe may be encoded by suitable apparatus to record the position of the carriage with respect to the elastomeric material. For example, inspection apparatus such as a transducer for measuring relative deflection, infrared scanners, moisture loss sensors, and ultrasound sensors are useful to measure the reaction of the elastomeric material as well as other symptoms of joint failure. A data collection apparatus is utilized to capture the results. Location data can optionally be gathered simultaneously via use of GPS (global positioning system equipment), to be transformed into two and or three dimensional graphical data, including GIS (geographical information systems), all to be included into the building owner's facilities management program. The performance and location data are then stored in a digital computer or other suitable data storage device or media. The results are produceable in various forms, such a graphic displays of the elastomeric joints inspected and the locales of substandard or failed portions thereof.

Our solution to providing a simple, low cost inspection device and method involves the use of a probe, such as a wheel of preselected size, which is supported by a transportable probe carriage or support structure. The carriage may support multiple testing devices, although in its most simple form, we have found that a wheel of preslected size which is floated at constant pressure in a hand held probe carriage may be effectively utilized to carry out the method. However, other carriage devices may be utilized in a probe carriage with enough inspection capability to efficiently scan a large structure.

Importantly by use of the inspection method described herein, excellent inspection accuracy and coverage is achieved in a cost effective manner. In contrast to inspection systems that have heretofore been commercially available, the novel apparatus and methods disclosed herein are adaptable to an easily transportable, rapidly executable, and reliable inspection method. The apparatus and methods are suitable for use by semi-skilled workmen, with resultant low inspection costs. The inspection system of the present invention is uniquely adapted to be utilized in a variety of applications, including some of which have heretofore been difficult to economically justify, such as 100 percent inspection of each joint in large commercial buildings. Further, the method and apparatus of the present invention allows the inspection process to be conducted in place, at any field location. Also, maintenance and repair costs can be reduced by way of correcting the defects found, without the necessity for wholesale replacement of joints which might become necessary from heretofore utilized partial inspection techniques.

By way of the present invention, we have developed a novel solution to the problem of the lack of a non-destructive test method of sealant joints in structures, and particularly in curtain wall buildings. The apparatus and methods employed are simple and easy to utilize. The ease of performing an inspection when utilizing the apparatus, and the opportunity to provide easily understood, complete graphical data presentations in an inspection report are unparalleled in the relevant inspection trades.

OBJECTS, FEATURES, AND ADVANTAGES

It is an object of the present invention to provide a simple inspection apparatus whereby it is feasible to easily and quickly inspect 100 percent of elastomeric joints in curtain wall buildings.

It is also an object of the present invention to provide a non-destructive sealant joint inspection system which is simple and inexpensive to manufacture.

It is yet another object of the present invention to provide an inspection device which is simple and portable so that non-destructive inspection can be easily performed wherever desired in the field.

It is still another object of the present invention to provide a device and method which is easy for semi-skilled workers to utilize for the purpose of evaluating the performance and quality of sealant joints in curtain wall buildings or other structures utilizing an elastomeric sealant joint.

It is yet another object to provide a method for detecting and inspecting sealant joints that have attributes that deviate below the minimum allowable specifications, such as may be established by project specifications, vendor guidelines, or by regulatory authorities.

It is yet another object to provide a method to correlate any particular sealant's hardness with the modulus of elasticity, which may, depending upon the specific sealant being tested, effectively act as a "rolling" durometer.

It is yet another important advantage that increased inspection rates may be provided at reduced cost, which dramatically decreases the potential for failure of weak or damaged sealant joints.

The above mentioned as well as other advantages and novel features of unique inspection devices, and of methods employing such devices for inspection of sealant joints, will all become evident and more fully appreciated from full evaluation and consideration of the following detailed description, as well as the accompanying tables and drawing figures.

BRIEF DESCRIPTION OF THE DRAWING

In order to enable the reader to attain a more complete appreciation of the invention, and of the novel features and the advantages thereof, attention is directed to the following detailed description when considered in connection with the accompanying drawings, wherein:

FIG. 8 is a perspective view of a conventional dial indicator when set up to measure the deflection of the elastomeric joint being inspected in response to the application of the substantially constant pressure probe thereto.

FIG. 9 is a schematic of a typical sealant joint, showing certain dimensions of importance in an inspection effort.

FIG. 10 provides a table of exemplary joint widths which were tested in one example of for calibration of the testing device described herein.

FIG. 11 provides data, as related to dimensions indicated in FIG. 15, of the dimensions of joints encountered in the application of an exemplary probe to a sealant joint at a preselected substantially uniform pressure.

FIG. 12 is a detailed data table indicating one example of deflections found during calibration testing of the inspection device described herein, wherein multiple passes were taken along a sealant joint, and the resultant deflections were recorded.

FIG. 13 provides a table of various probe roller wheel sizes that have been evaluated for use in the inspection device disclosed herein.

FIGS. 15 through 18 show, in both graphical and in tabular format, the relationship of the average deflection of a test specimen in a joint relative to the size of the wheel utilized in deflection testing for a specific elastomer test sample.

FIG. 15 shows the impact of wheel size relative to deflection for a one inch wide joint.

FIG. 16 shows the impact of wheel size relative to deflection for a five eighth's inch wide joint.

FIG. 17 shows the impact of wheel size relative to deflection for a one-half inch wide joint.

FIG. 18 shows the impact of wheel size relative to deflection for a seven-eighths inch wide joint.

FIG. 19 provides a summary, in tabular form, of the wheel sizes found to be allowable for various joint widths, for a particular sealant tested.

The foregoing figures, being merely exemplary, contain various elements that may be present or omitted from one embodiment of an inspection device or one variation of an inspection method, depending upon the circumstances. An attempt has been made to provide the information in the figures in a way that illustrates at least those elements that are significant for an understanding of the various embodiments and aspects of the invention. However, various other elements of the inspection device, its calibration methods, and inspection methods are also shown and briefly described to enable the reader to understand how various optional features may be utilized in order to provide a high quality, high performance, cost effective non-destructive testing device and method for sealant joints.

DETAILED DESCRIPTION

Figure 1:
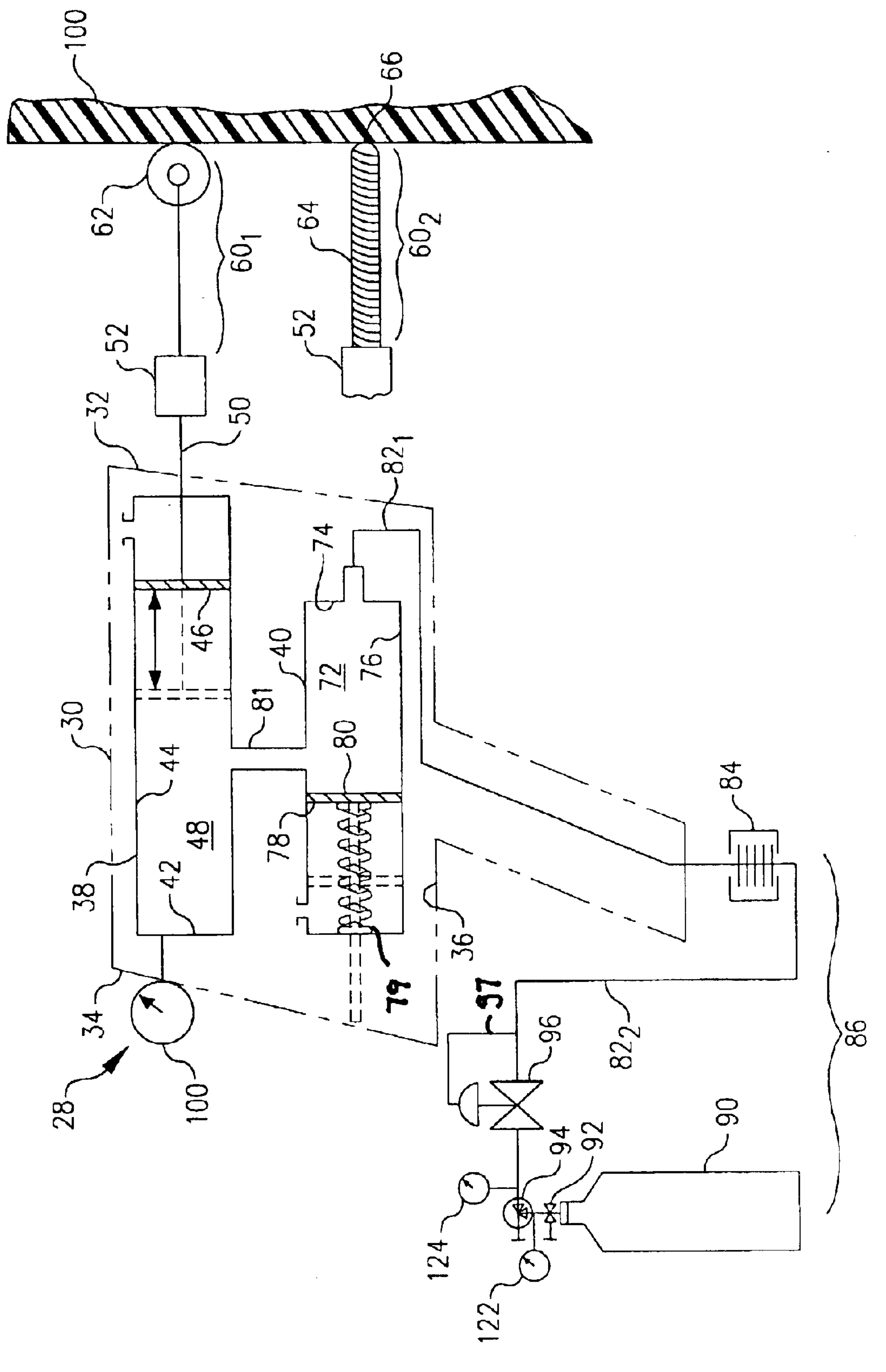
FIG. 1 is a schematic diagram of one embodiment of the inspection apparatus of the present invention; however, the alternative use of a wheel type probe and of a blunt elongated, non-rolling probe are shown, as acting against a sealant in a joint.

Attention is directed to FIG. 1, where one embodiment of a suitable non-destructive testing device for sealants is schematically illustrated. A probe carriage 30 is shown in broken lines. Probe carriage 30 has a front 32 and a rear 34 and is provided with a frame 36 in which a first fluid cylinder 38 and a second fluid cylinder 40 are secured. End wall 42, sidewall 44, and piston 46 define a first fluid chamber 48 within first fluid cylinder 38. Piston 46 has connected thereto a probe shaft 50 which extends forward from first fluid cylinder 38. Probe shaft optionally includes a quick connect fitting 52 for interchange of probes 60. A first probe $\mathbf{60_1}$ is shown utilizing a probe roller wheel 62 design. Alternatively, second probe $\mathbf{60_2}$ may be provided utilizing a non-rolling indenter 64 having a working end 66.

Second fluid cylinder 40 contains a second fluid chamber 72 defined between end wall 74, sidewall 76, and piston 78. First 38 and second 40 fluid cylinders may be provided by any convenient fluid cylinder configuration. However, one usable device has been located as Lin-Act Series C85 stainless steel body air system cylinders, sold by Fluid Connector Products, Inc., 20581 Painters Street, Bend, Oreg. 97701. Piston 78 is biased by means such as spring 79 against movement responsive to pressure exerted on face 80 of piston 78. The first fluid chamber 48 and the second fluid chamber 72 are in fluid communication via interconnecting line 81. A fluid supply regulated at substantially constant pressure is provided to second fluid chamber 72 via fluid supply line $\mathbf{82_1}$. As indicated in this FIG. 1, a quick connect fitting 84 is utilized so that the probe carriage 30 may be quickly removed from a fluid supply 86. When a pressurized gas is utilized as a fluid source, a gas supply tank 90 with shutoff valve 92 and gas pressure regulator 94 are utilized. Here, for emphasis, a separate control valve 96 is shown with feedback loop 97 for maintaining a substantially constant pressure via fluid supply line 82 (including supply line portions $\mathbf{82_1}$ and $\mathbf{82_2}$), but those of skill in the art will recognize that a conventional pressurized tank gas pressure regulator 94 may suffice in many applications. For convenience of the operator of the inspection device 28, the probe carriage 30 optionally includes a pressure gage 100 for easy verification of the pressure within the interconnected first 48 and second 72 fluid chambers.

And, although a gas (such as carbon dioxide or other convenient or economical gas source) may be utilized as just described for maintaining relatively constant fluid pressure supply, the invention is not restricted to such constant pressure fluid supply mechanisms. Indeed, in one embodiment, the invention should be considered to include as a key ingredient the delivery of a substantially constant force at the working end of a probe, and therefore other devices and methods may be employed other than constant fluid pressure, and still be within more generalized application of the teachings and claims hereof.

Figure 14:
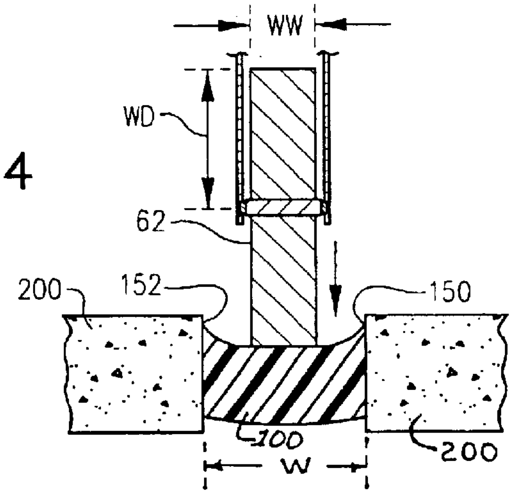
FIG. 14 illustrates the dimensions of an exemplary probe roller wheel as it deflects a hypothetical sealant joint.

As will be further explained herein below, in an inspection method employing the probe carriage 30 or similar device, the object of the method is to stress the center of a joint sealant bead 100, by depressing the center of the sealant joint bead 100 with a probe, such as probe roller wheel 62 or working end 66 of probe 64, to create an elongation strain on the sealant joint 100. The pressure applied by the probe is adjusted to conform to the range of suitable properties of the sealant formulation and joint geometry being tested, as necessary to produce a preselected elongation E of the sealant joint 100. One convenient testing method involves a 50% elongation of the sealant joint. In one embodiment of the method, the probe may be passed along the full longitudinal length of the sealant joint 100. Also, in one embodiment of the method, the probe footprint width (width WW if a probe roller wheel 62 is utilized of having a wheel diameter WD, as shown in FIG. 14) should be approximately ⅓ of the width W of the sealant joint 100.

Figure 2:
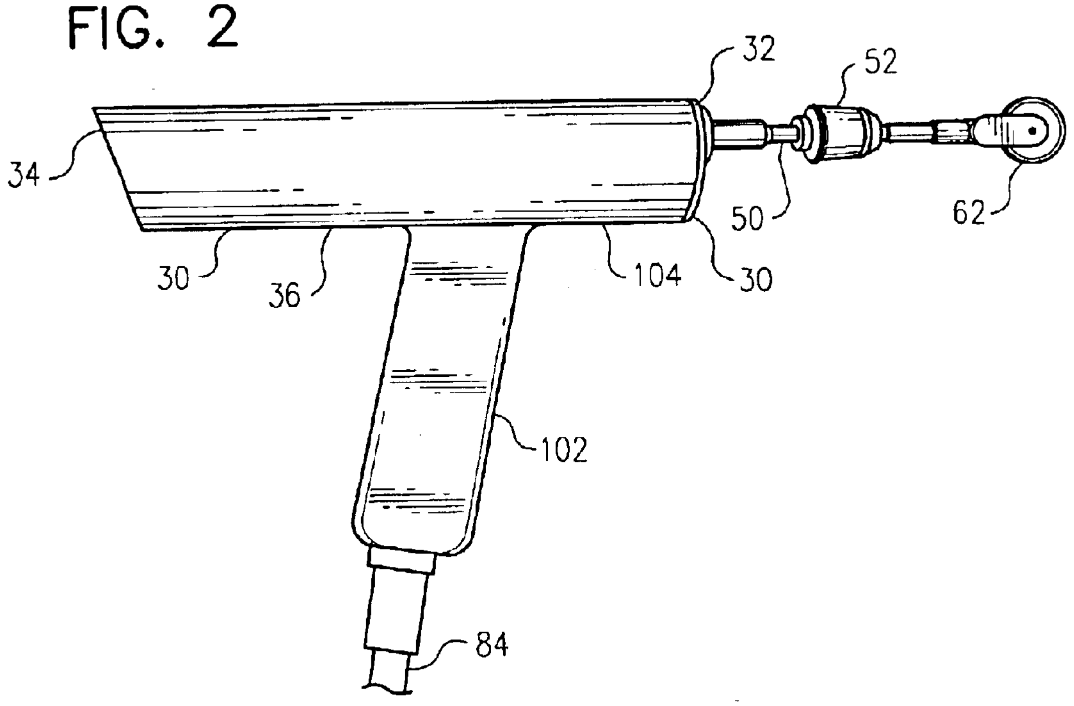
FIG. 2 is a side view of one embodiment of a probe carriage device, showing use of a quick disconnect gas fitting, a quick disconnect probe fitting, and the basic frame, handle, and cover of this hand held embodiment.

Turning now to FIG. 2, a side view of the probe carriage 30 is shown, having a probe roller wheel 62 affixed thereto. For operator convenience, a handle 102 is utilized extending obliquely downwardly and rearwardly from the lower portion 104 of frame 36. The handle 102 is better seen in FIG. 4

Figure 3:
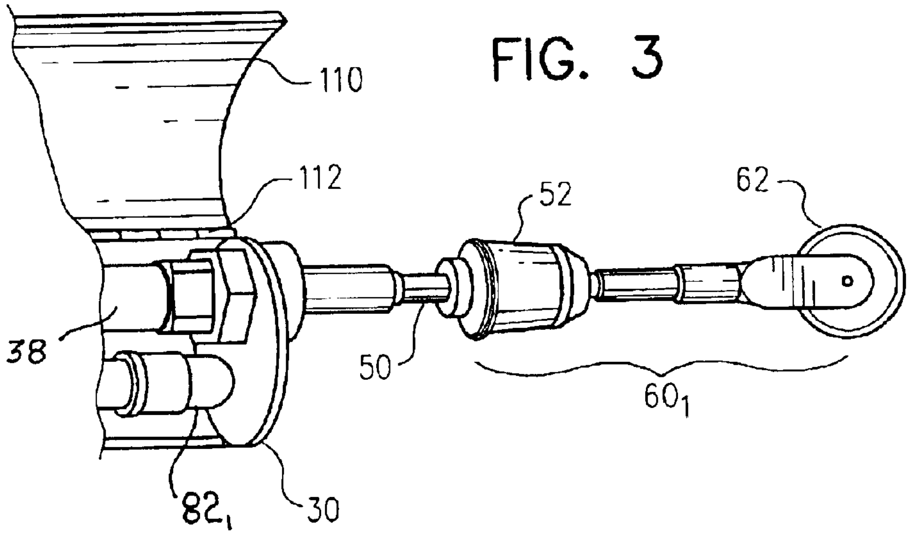
FIG. 3 is a close up of a portion of the probe carriage device just illustrated in FIG. 2, now showing the frame cover in an open position, and further showing the probe shaft quick disconnect fitting, as well as one size of probe wheel which can be utilized in the practice of the non-destructive testing method taught herein.
Figure 4:
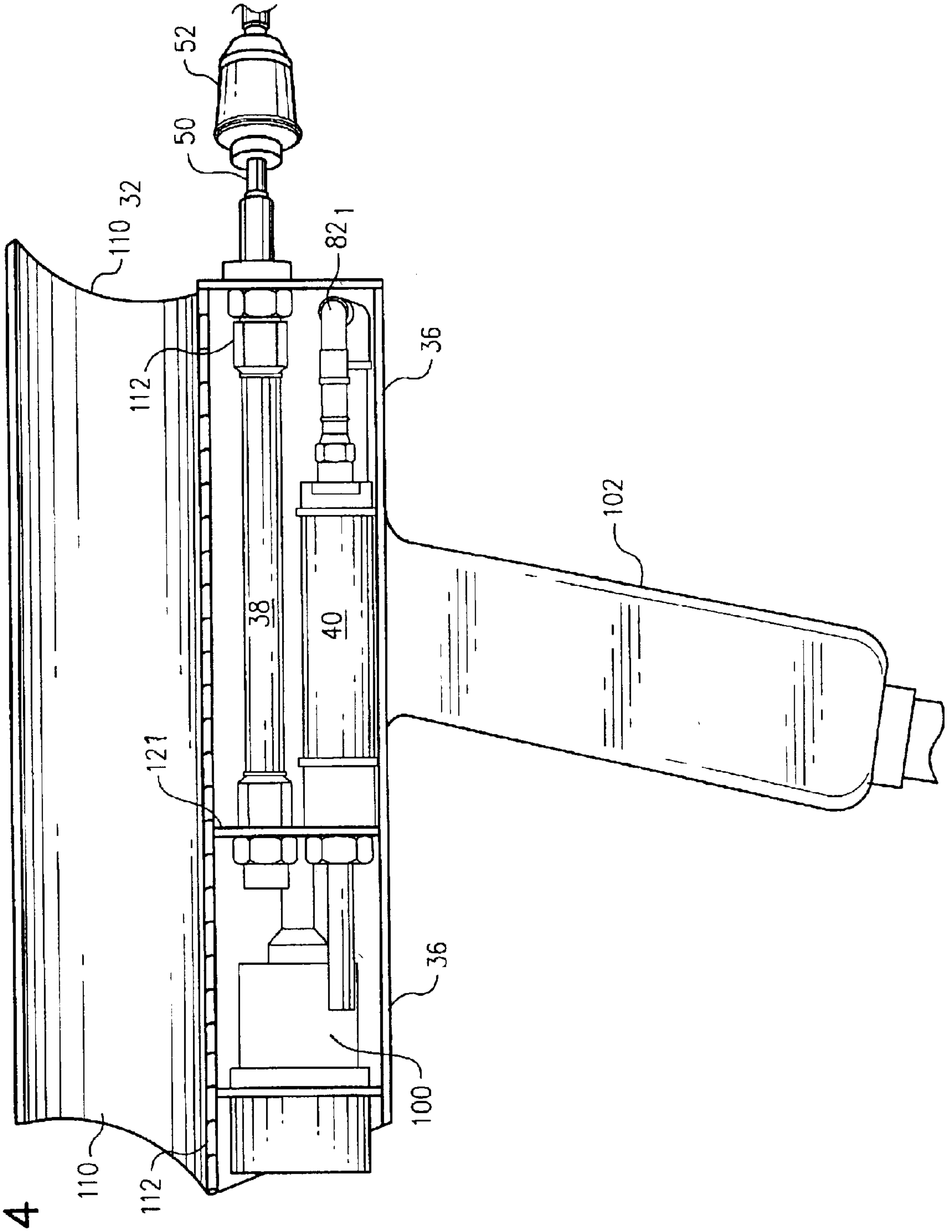
FIG. 4 is a side view of the interior of the frame case, showing first and second fluid cylinders as utilized for maintaining a constant working force or pressure on the working end of a selected probe.

As shown in FIGS. 3, and 4, a preferably arcuate portion of a tubular cylinder provides a shaped cover 110 for the probe carriage 30. In these figures, the cover 110 is shown in the open position, and the hinge 112 connecting cover 110 to frame 36 is seen.

In FIG. 4 a side view of the interior of the frame case 36 is provided, showing first 38 and second 40 fluid cylinders as utilized for maintaining a constant working force or pressure on the working end of a selected probe 60. The relative size of components in one exemplary embodiment of carriage probe 30, and particularly of first 38 and second 40 fluid cylinders is shown in FIG. 4. Further, fluid supply line $\mathbf{82_1}$ is shown provided in a fluid tight connection to the second chamber 72 within second fluid cylinder 40.

FIG. 4 also shows the transversely oriented mount portion 121 of frame case 36 which is utilized for securing the first 38 and second 40 fluid cylinders, as well as the pressure gage 100 for determining the pressure within the substantially constant pressure chamber 48. FIG. 3 additional provides a further close-up of the front interior portion of the frame case 36 and internal components as just illustrated in FIG. 6, but now showing the hinged frame cover 110, and the fluid piping $\mathbf{82_1}$ for supply of equalization fluid to the second or lower fluid cylinder 40 from a remote fluid supply.

Figure 5:
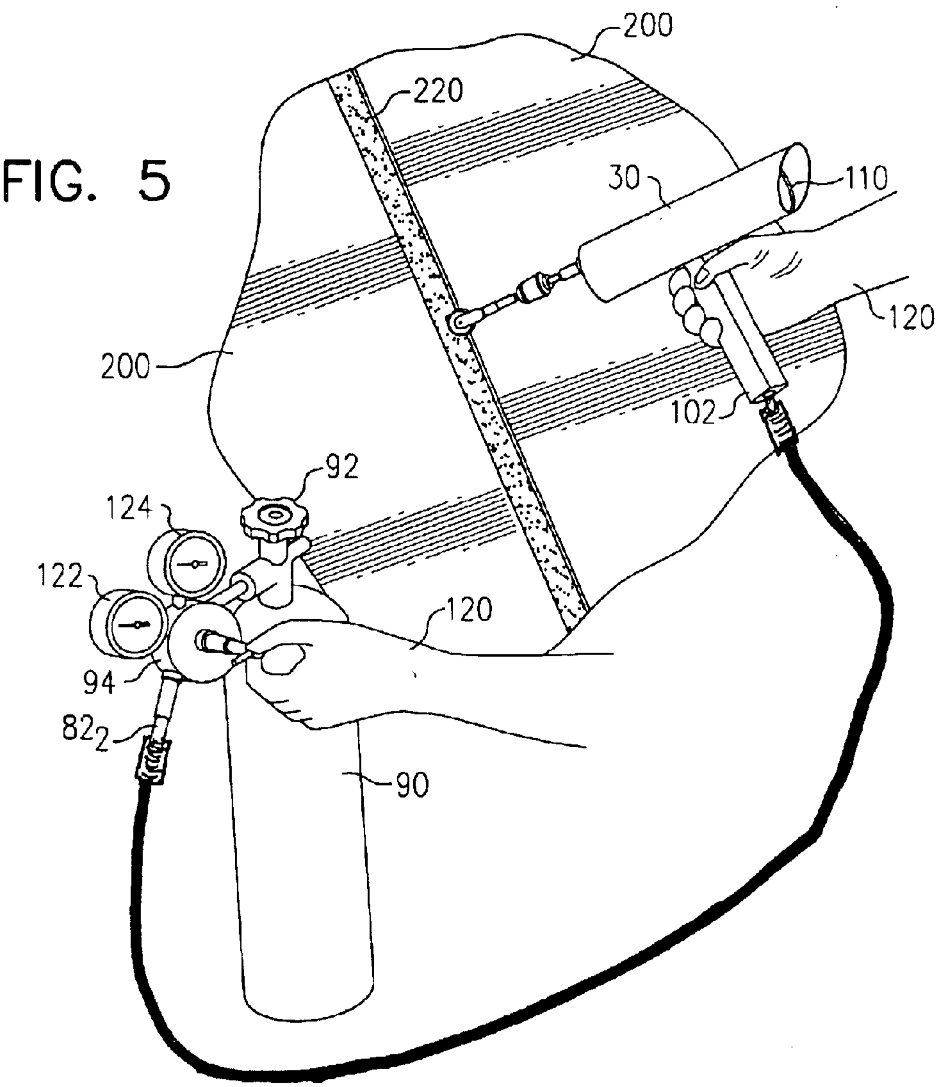
FIG. 5 illustrates the use of a compressed gas as a working fluid, and shows a workman adjusting the supply pressure to the substantially constant pressure chamber while observing the actual pressure on the pressure gage, while the testing device has the probe engaged against a sealant joint in a building.
Figure 6:
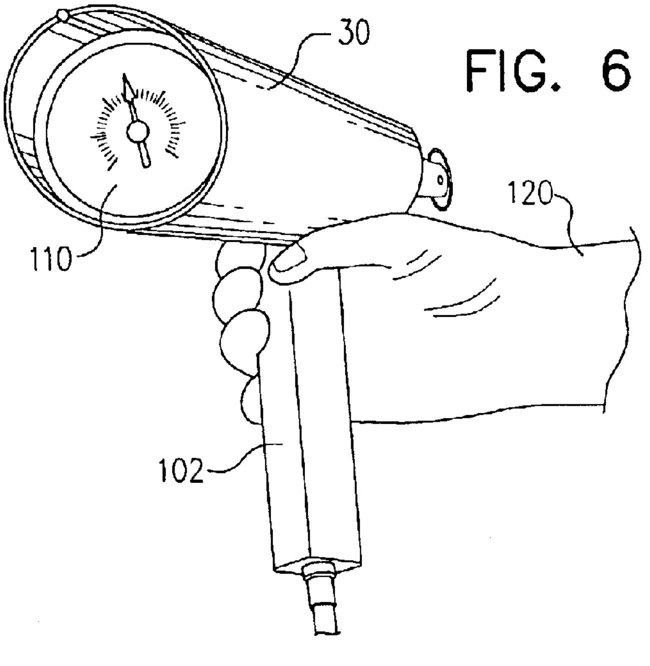
FIG. 6 provides a close-up of one desirable location of a pressure gage within the rear of the frame casing.

In FIG. 5, the use of a compressed gas as a working fluid is illustrated. Pressurized gas in tank 90 is provided through manual shutoff valve 92 and thence through a manually adjustable gas pressure regulator 94, and thence outward through gas line $\mathbf{82}_2$. An inspection technician 120 is shown adjusting the supply pressure at regulator 94 to a preselected substantially constant pressure for supply of gas at the preselected pressure to constant pressure chamber 72. Inlet pressure gage 122 and outlet pressure gage 124 are normally provided at gas pressure regulator 94. Since chamber 48 and chamber 72 are in fluid communication, pressure equalizes therebetween and the pressure in both chambers is essentially identical (assuming line 81 is adequately sized), and the pressure can be read from gage 100, as shown in FIG. 6.

Returning now to FIG. 1, operation of the apparatus 28 can be further addressed. Basically, the testing apparatus 28 is designed to provide a continuous strain to a bead of joint sealant 100 by using an intending probe 60, preferably either of the roller type $\mathbf{60}_1$ or of a solid non-rolling indenter type $\mathbf{60}_2$, as discussed above. In the embodiment illustrated, a substantially constant force F is provided against sealant joint 100 by virtue of maintaining a substantially constant force acting on probe shaft 50, which in turn is consequently directed during testing at constant force F against sealant joint 100. In the embodiment illustrated, this is accomplished by use of a constant pressure on piston 46 which drives probe shaft 50. This pressure stress centered on the sealant joint 100 provides a strain on the adhesive bond at the first 150 and second 152 edges of the sealant joint 100, as indicated in FIG. 14. Note that although this device is termed non-destructive, this procedure may result in an adhesive failure of a deficient seal at either first 150 or second 152 edges. However, by proper selection of a preselected pressure, the applied stress should not provide a strain that results cohesive failure in the sealant. In other words, the test results should either be (a) adhesive failure, or (b) no failure of the sealant. We have found that one desirable applied constant testing force is one that is calibrated to provide elongation of the sealant joint to about 50% of the elongation E value that would result in adhesive failure. Thus, it is important to calibrate the testing device 28. This is accomplished easily with a mock-up or off-site test bed using the appropriate sealant (e.g., the sealant used in manufacture of the sealant joints to be tested) and joint geometry, particularly joint width. In one method of implementing the inspection techniques, it may be appropriate for the sealant manufacturer to complete the calibration process for their particular sealant so that the published data is controlled and validated by the manufacturer.

Figure 7:
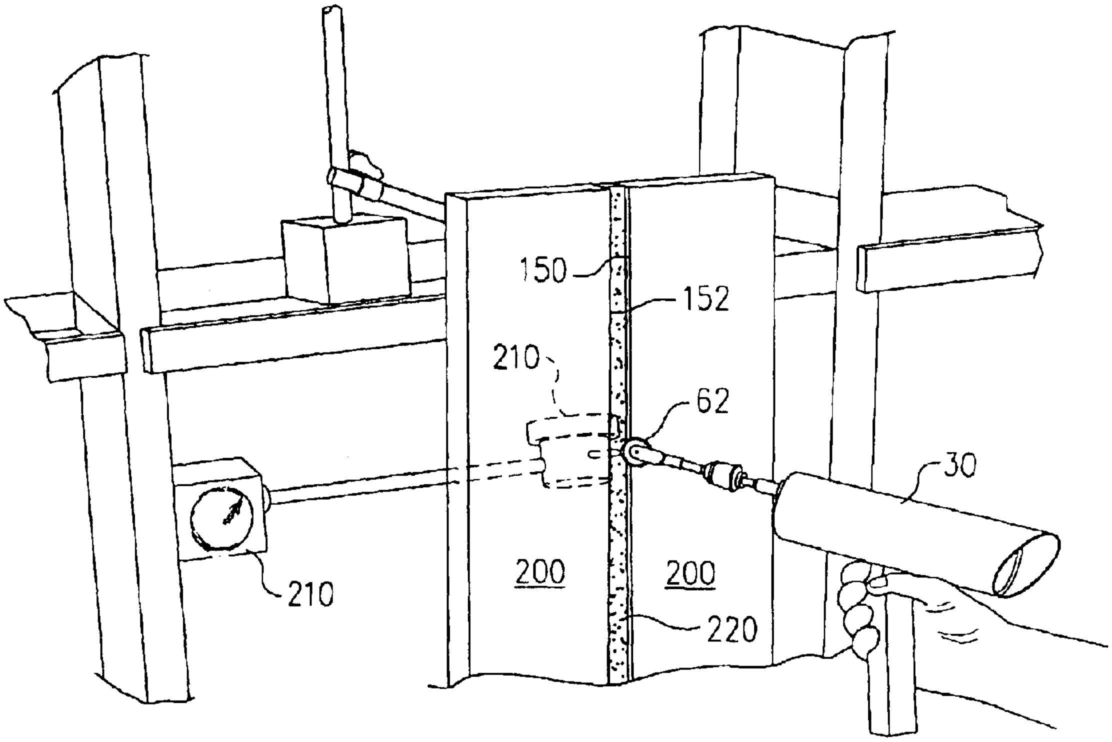
FIG. 7 shows one idealized test specimen on which calibrations were taken of one embodiment of the inspection device disclosed herein, wherein two substrate panels (here wood panels) were positioned with a substantially uniform gap therebetween, and the gap was closed utilizing a preselected elastomeric sealant which was allowed to cure before testing was started.

As seen in FIGS. 7 and 8, a pair of suitable substrates 200 are provided adjacent each other to provide a substantially uniform gap therebetween. A dial indicator 210 is utilized in conjunction with a force gage to determine the force necessary to elastically deform the "perfect" sealant bead 220 having a thickness T (see FIG. 9) by a distance E of 50%. This technique provides a starting point for calibrating the testing device 28. After such calibration, then the device 28 can be simply set up in the field at the preselected internal pressure in chambers 48 and 72. If necessary the process can be repeated until a statistically coherent and usable data set is produced. Note particularly that it is usually necessary to calibrate the device for multiple joint widths, since joint width, depth, and sealant elastic modulus are all variables that require, in combination, different pressures to achieve the desired result, specifically a preselected percent of elongation (such as 50%). In reality, all joint beads are not "perfect" so the goal is to utilize a good sealant joint bead for calibration purposes, and then to apply the selected uniform stress at the center of the joint bead to induce a uniform strain on the adhesive joints at the edges of the sealant joint. Sometimes, the elongation at the left side of a sealant joint ($E_L$) may be different than the elongation along the right side of a sealant joint ($E_R$), as noted in FIG. 9, which may be observed visually along a failing joint sealant system.

Importantly, device 28 can be calibrated to any selected sealant composition, since the calibration process described above and illustrated in FIGS. 7 and 8, can be simply repeated for any given sealant composition. And, of course, the inspection device 28 is adjustable with respect to internal pressure, and thus force applied by the probe 60. In those cases where the sealant changes elastic modulus with temperature variation, an acceptable set of temperature ranges can be established for testing. For example, a calibration set could be scaled to ranges of temperatures, such as 30° F., 50° F., 70° F., and 90° F. (+/− X degrees each) for a class, brand, or specific formulation of sealants, as applicable. Also, if the Shore A hardness value of a particular joint seems higher than anticipated, a durometer reading should be taken. Then, if the sealant reads, for example, 10% higher in durometer than anticipated, it can normally be presumed that the sealant is no longer able to perform at its intended modulus of elasticity. Accordingly, if the decision is to continue with the evaluation, then the pressure required for deflection should be appropriately adjusted to the deviation determined by the durometer readings.

Attention is directed to FIG. 9, where a typical joint is dimensioned for reference. One range of possible wheel widths for various embodiments of testing device 28 are suggested in FIG. 13. For clarification, the application of a specific wheel 62 to a specific sealant joint is shown in FIG. 14. Overall, we have found it advantageous to utilize a ratio of roller wheel width WW to joint width W of about 1 to 3. In other words, in one embodiment, the joint itself is about 3 times as wide as the probe roller wheel 62 provided.

For ease of hand held utilization, probe carriage 30 as illustrated in one embodiment herein is easily hand carried by workmen. In such an embodiment, probe carriage 30 it weighs only about 5.1 pounds, even utilizing a stainless steel frame case and metal fluid cylinders.

EXAMPLE

A Dow Corning 795 bronze sealant was applied between wood battens to different joint configurations and different joint widths. The sealant joint was allowed to cure for two months prior to testing. The samples were not exposed to exterior weather conditions at any time. The sealant specimens were approximately 24" long. No special care was taken when applying the samples, as one of the features of the invention is to recognize variations within joints.

The samples were mounted on to a test stand that allowed for the application of dial indicators with follow-up hands at three locations on each sample (top, center, and bottom). Deflection indicators were centered within the joint widths and set to zero. The readings were reported in hundredths of an inch (see FIG. 12). The samples were measured, after testing, to identify the joint configuration at each point of measurement, and to assist in the analysis of the deflection readings obtained when different pressures and different probe roller wheels were utilized along the length of each sample. The joint widths and depths are shown in FIG. 11.

Figure 15:
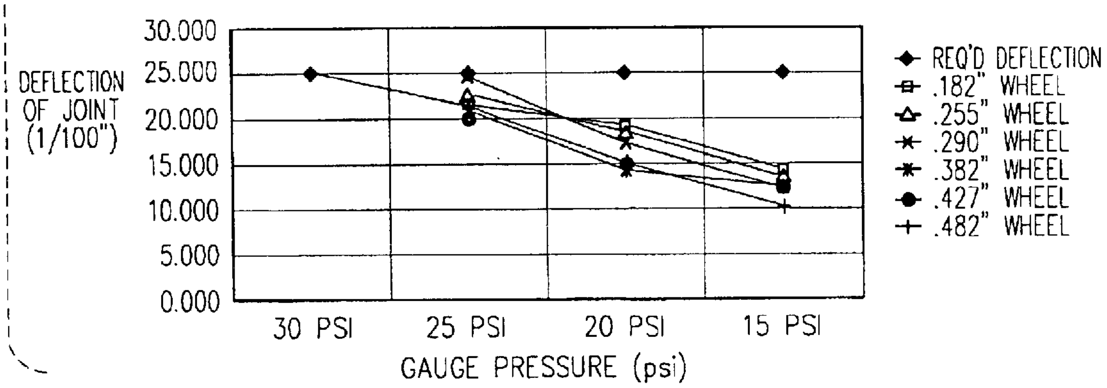

A first calibration data set is provided in FIG. 15, where this particular sealant, namely Dow 795 (available from Dow Corning) has been evaluated for a specimen joint A of 1 inch width W.

Figure 16:
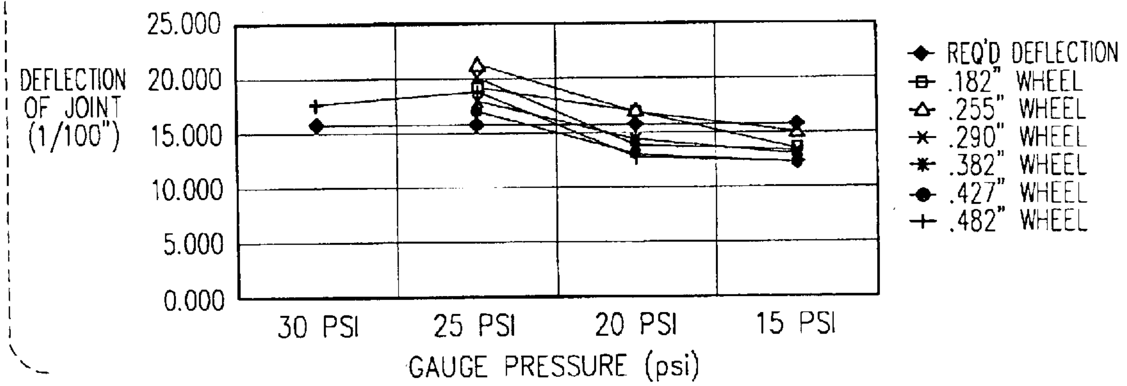

A second calibration data set is provided in FIG. 16, where this particular sealant, namely Dow 795 (available from Dow Corning) has been evaluated for a specimen joint B of ⅝ inch width W.

Figure 17:
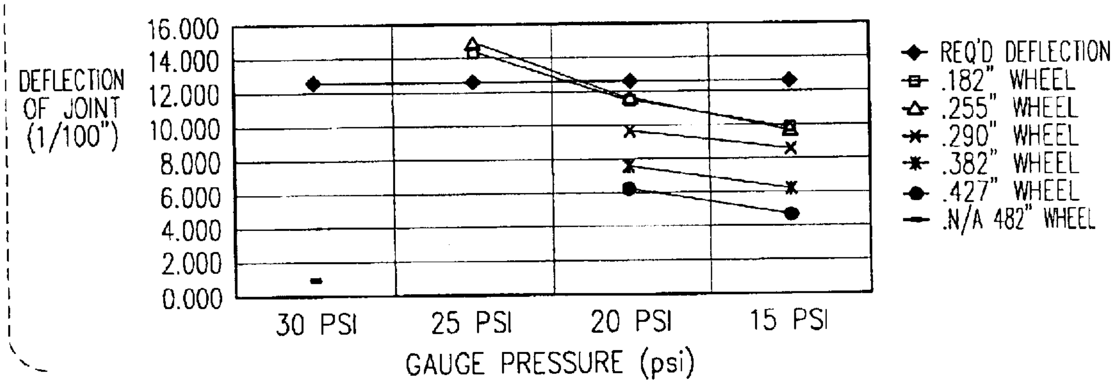

A third calibration data set is provided in FIG. 17, where this particular sealant, namely Dow 795 (available from Dow Corning) has been evaluated for a specimen joint C of ½ inch width W.

A fourth calibration data set is provided in FIG. 19, where this particular sealant, namely Dow 795 (available from Dow Corning) has been evaluated for a specimen joint D of ⅞ inch width W.

Importantly, the probe carriage 30 illustrated herein may be utilized with additional inspection and data gathering equipment. For example, the use of video and/or web cameras, infrared (energy loss sensors), moisture sensing, and ultrasound testing sensing equipment would also enhance joint inspection and evaluation data. Any of the equipment can be utilized with data link and data logging apparatus, such as found in conjunction with data acquisition programs utilized in a general purpose computing unit. Further, various mapping and locating techniques, such as GPS (global positioning system equipment), or GIS (geographical information systems) could be coupled with an effective data output or graphical and statistical presentation system, for clear analysis of joint systems structures, and particularly on curtain wall buildings.

For purposes of simplicity and ease in understanding the operation, the device 28 in the above discussion has shown the apparatus operating in stand-alone mode with only one probe and no additional sensors. However, the concepts described herein will be further elucidated hereinbelow, and such further and additional features should be considered within the scope and coverage of the teachings hereof.

Figure 20:
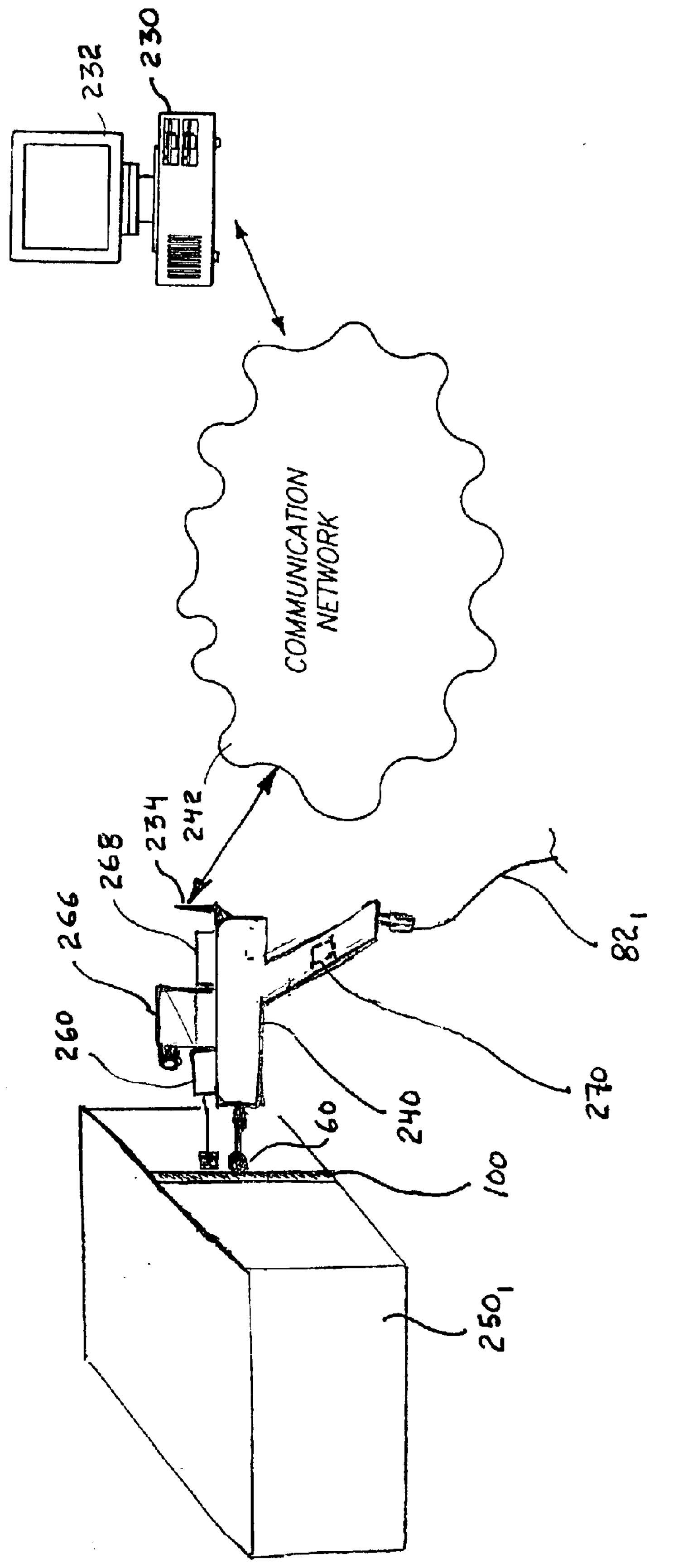
FIG. 20 illustrates the use of a probe carriage for testing a sealant joint in a building wall, showing the use of a remote communication device to provide data and test results from a first test probe, a separate test device such as infrared or ultrasound, as well as from a camera and a global positioning system (GPS), in order to map the status of various joints in a building structure.
Figure 21:
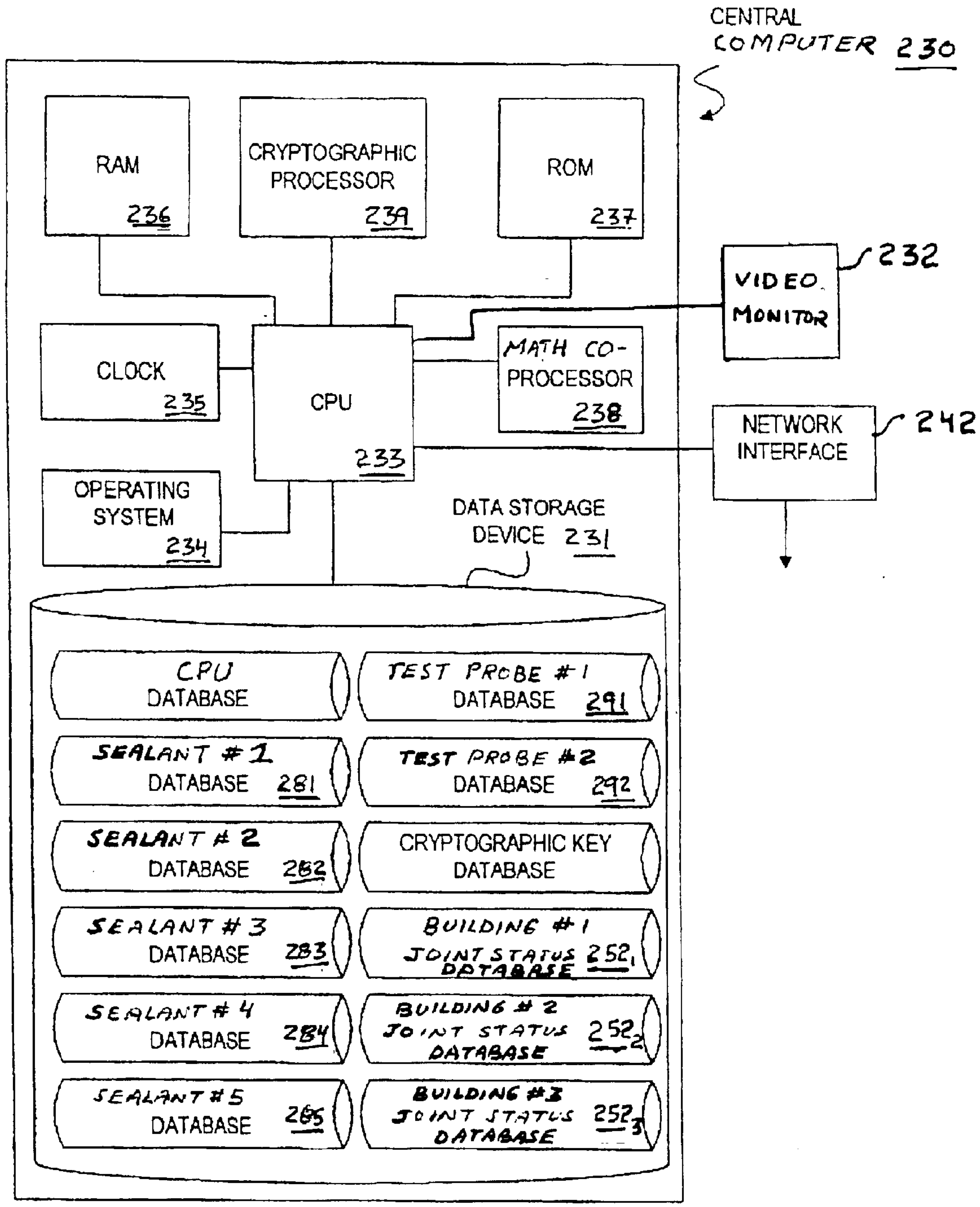
FIG. 21 illustrates the use of a central computer for storing test calibration data bases for various sealants, and for storing calibration and physical data for various test probes, and for storing data collected and reports developed from such data for various building structures.
Figure 22:
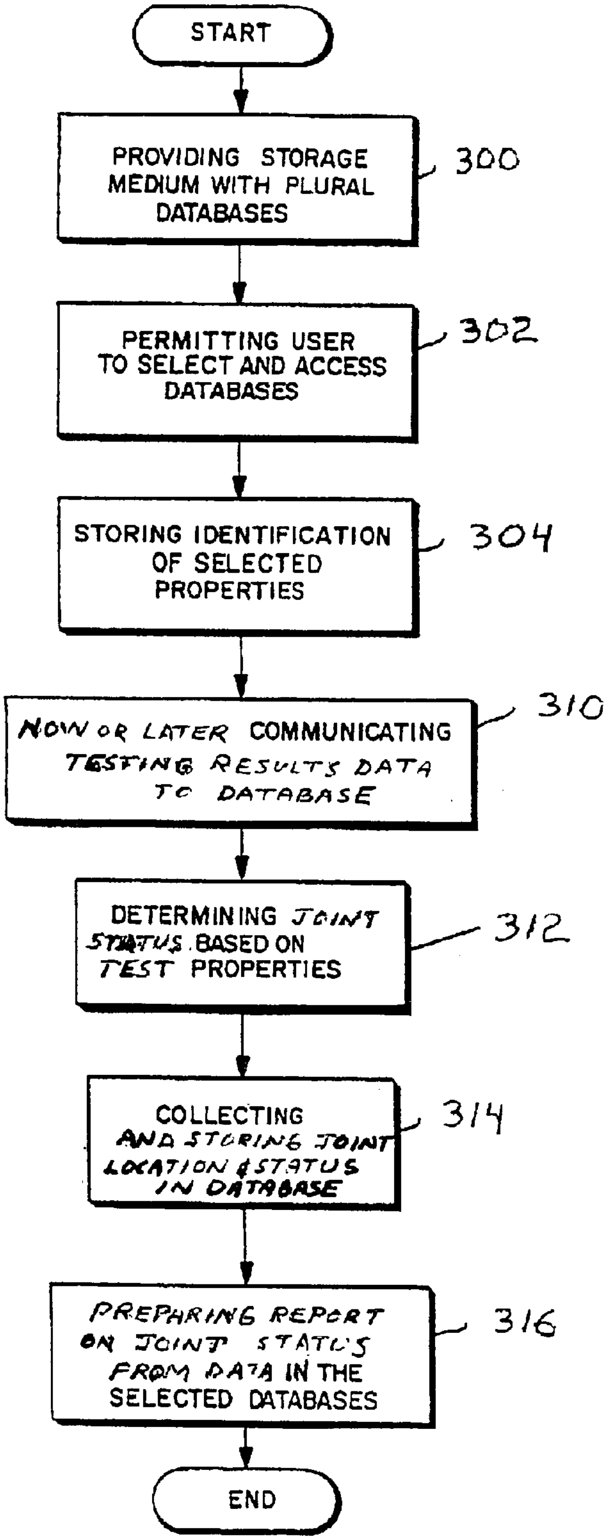
FIG. 22 illustrates the steps in one method of using a test device for testing sealant joints, including providing a central computer having a storage medium with databases, communicating test results from a test probe or other data output device such as a camera or GPS receiver to the database, determining the properties of the joint being tested, and then generating a report of the status of joints in a building system from the data in the various databases.

Importantly, any discontinuities in the sealant joint 100 (for adhesion, or heat loss, or moisture loss, or thickness measurement, etc.) can be easily combined in digital or other form and captured in a data gathering system such as a central computer 230 as generally depicted in FIGS. 20, 21, and 22. Such data can be displayed in real time such as on video monitor 232 or recorded in individualized databases for later analysis and display. Flaws in adhesion, heat loss, moisture loss, thickness, etc., can be sorted into the correct locations by programming means in a digital computer 230, and recorded in appropriate data files. Appropriate cabling (not shown) or wireless communication technology 234 can be utilized to connect the inspection system test probe 240 via a suitable communication network 242 to the remote central computer 230. The computer 230 can use the gathered information to store averaged measurements at regular intervals along each sealant joint 100 being inspected in a selected building $250_1$, $250_2$, $250_3$, etc. in a corresponding building joint status database $252_1$, $252_2$, $252_3$, etc., as appropriate.

As depicted in FIG. 20, the testing device 240 can include, in addition to test probe 60 as above described, a secondary sensing device 260. Such secondary sensing device may be (a) an infrared sensing device, (b) a moisture sensing device, (c) an ultrasound sensing and testing device, or (d) another non-destructive testing device that provides a digital output signal. Additionally, a video camera 266 can be provided to simultaneously photograph and test a particular sealant joint section. And, a mapping system, such as one including the use of a global positioning (GPS) receiver 268 can be utilized to provide data as to the location of the testing device 240. For example, the probe carriage can include as a secondary sensing device 260 an ultrasonic signal generator that provide a series of acoustical pulses and an ultrasonic signal transducer to convert a received series of reflected acoustical signals from the sealant joint to a corresponding set of acoustical pulses, as well as a means to clock and to drive the acoustical transducers, so that the sensing device 260 provides sealant joint 100 thickness data in response to each transducer pulse. In this manner, the computer 230 can be programmed to record the thickness signal, as well as the location and displacement encoder signal, so as to store data regarding the thickness of a sealant joint by specific location.

Thus, any one of a selected set of on board digital data output devices can be provided on a suitable testing device 240, and if desired, a digital recording device 270 can also be utilized in testing device 240 to eliminate the need to constantly transmit data via network 242 to the central computer 230, so that such data can be sent periodically, in an intermittent pattern over time (i.e., later), rather than real time, as in a data packet switching network sense (i.e., now, although data packets may be sent in bunches). It can be readily understood that a network 242 may not be necessary in some situations, and thus data can be directly communicated to computer 230. Also, those of ordinary skill in the art and to whom this specification is addressed will readily understand that a typical general purpose computer 230 may include a data storage system 231 such as a hard disc drive, a central processing unit or CPU 233, a software operating system 234, a clock system 235, random access memory (RAM) 236, and read only memory (ROM) 237, and optionally a math coprocessor 238 to speed processing of large data sets. Increasingly, the use of a cryptographic processor 239 is common for making data sets unusable to unauthorized recipients.

With respect to data storage and manipulation in central computer 230, a variety of schemes can be utilized with the teachings herein. For example, as described above, calibration results for a various sealants, such as sealant #1, sealant #2, sealant #3, sealant #4, and sealant #5 can be separately stored in individualized databases such as 281, 282, 283, 284, and 285, or such data may be complied in a larger single sealant database. Also, the physical size or other data for selected probes 60 may be stored in a database 291 for test probe #1, and in database 292 for test probe #2, as shown. Alternately, data for electronically driving or for interpreting output of one or more of selected secondary sensing devices 260 can be stored as necessary in such databases as database 292, or in additional similar but separate databases.

Thus it can be seen that a computer 230 is provided as noted in block 300 of FIG. 22 with plural database capability for storage of necessary joint sealant calibration data, as well as for primary test probe 60 data and secondary sensing devices 260. When a selected building 250 is to be tested, the user selects and accesses the appropriate databases as noted in block 302 of FIG. 22. Then, as noted in block 304 of FIG. 22, the identified properties of the joint sealant to be tested, or other appropriate data, is stored in RAM 306 or other data storage location as necessary in a selected computer 230. As test probe 240 is used on building 250, data generated is communicated, now or later, to an appropriate database in computer 230, and/or, displayed in real time on video monitor 232, as noted in block 310 if FIG. 22. Thus, it is possible to determine the status of a sealant joint 100 based on the test properties indicated by test data, as noted in block 312 of FIG. 22. Selected data is thus collected and stored, with respect to joint status and location, as noted in block 314 of FIG. 22. Thus, from such data displayed or collected and stored, it is possible to prepare a report on joint status and location from data gathered and stored, either temporary or permanently in the selected database, as indicated in block 316 of FIG. 22.

It is to be appreciated that the various aspects and embodiments of the non-destructive testing apparatus described herein, and the method of using the same, is an important improvement in the state of the art of inspection of elastomeric seals, especially in curtain wall building structures. Although only a few exemplary embodiments have been described in detail, various details are sufficiently set forth in the drawings and in the specification provided herein to enable one of ordinary skill in the art to make and use the invention(s), which need not be further described by additional writing in this detailed description. Importantly, the aspects and embodiments described and claimed herein may be modified from those shown without materially departing from the novel teachings and advantages provided by this invention, and may be embodied in other specific forms without departing from the spirit or essential characteristics thereof. Therefore, the embodiments presented herein are to be considered in all respects as illustrative and not restrictive. As such, this disclosure is intended to cover the process, methods, and products described herein and not only structural equivalents thereof, but also equivalent structures. Numerous modifications and variations are possible in light of the above teachings. It is therefore to be understood that even within the scope of the claims herein, the invention(s) may be practiced otherwise than as specifically described herein. Thus, the scope of the invention(s), as set forth in such claims, and as indicated by the drawing and by the foregoing description, is intended to include variations from the embodiments provided which are nevertheless described by the broad interpretation and range properly afforded to the plain meaning of the claims.

And, of course, while the invention has herein been described and illustrated in connection with an exemplary "manually portable" non-destructive inspection apparatus and method, the apparatus need not be "manually portable," but can constitute a more complex robotic inspection apparatus that can efficiently inspect large facilities, and, in unique cases, may even be applicable to inspection machines to which material to be inspected can be brought.

What is claimed is:

1. An apparatus for testing elastomeric joints, said joints comprising a length of sealant spanning a gap between adjacent substrates, said apparatus comprising:

(a) a frame (b) a first fluid cylinder, said cylinder comprising (i) a first end wall, (ii) a first tubular cylinder wall (iii) a first piston (iv) a first shaft, said first shaft response to movement of said piston, said first shaft having a probe connection portion;

(c) a probe, said probe affixed to said probe connection portion;

(d) a second fluid cylinder, said second fluid cylinder having an internal pressure equalization chamber defined by (i) a second end wall, (ii) a second tubular cylinder wall (iii) a second piston (e) a fluid supply port for receiving a substantially constant pressure fluid supply to said internal pressure equalization chamber; and (f) wherein movement of said first piston transfers fluid pressure to said internal pressure equalization chamber of said second piston, thereby maintaining a substantially constant pressure on said first piston, and thus a substantially constant reaction force on said probe.

2. The apparatus as set forth in claim 1, further comprising a pressure gage connected to said substantially constant pressure internal chamber.

3. The apparatus as set forth in claim 1, wherein said frame further comprises a handle, said handle adapted for manual support and use by a single workman.

4. The apparatus as set forth in claim 1, wherein said probe comprises a rolling wheel of preselected width WW.

5. The apparatus as set forth in claim 4, wherein said probe comprises a rolling wheel of preselected diameter WD.

6. The apparatus as set forth in claim 1, wherein said probe comprises a non-rolling indenter.

7. The apparatus as set forth in claim 6, wherein said indenter comprises a smoothly radiused working end.

8. The apparatus as set forth in claim 1, wherein said frame further comprises a cover, said cover moveable between an open position, wherein internal components are accessible, and a closed position, wherein internal components are not accessible.

9. The apparatus as set forth in claim 8, further comprising a hinge, and wherein said cover is hinged to said frame.

10. The apparatus as set forth in claim 1, further comprising a first gas supply line, said gas supply line having a delivery end affixed to said second cylinder and in fluid communication with said substantially constant pressure chamber.

11. The apparatus as set forth in claim 10, wherein said first gas supply line comprises a second end, and wherein said frame further comprises a handle, and wherein said second end exits said frame at said handle.

12. The apparatus as set forth in claim 11, wherein said first gas supply line further comprises, at said second end, a quick disconnect fitting.

13. The apparatus as set forth in claim 1, further comprising an infrared sensing device.

14. The apparatus as set forth in claim 1, further comprising a moisture sensing device.

15. The apparatus as set forth in claim 1, further comprising a ultrasound sensing and testing device.

16. The apparatus as set forth in claim 1, further comprising a video camera.

17. The apparatus as set forth in claim 1, further comprising a global positioning position receiver.

18. The apparatus as set forth in claim 1, further comprising an on/board digital data output device.

19. The apparatus as set forth in claim 1, further comprising a wireless data transfer device.

20. The apparatus as set forth in claim 1, further comprising a digital data recording device.

* * * * *